United States Patent [19]
Nakamura et al.

[11] Patent Number: 6,019,763
[45] Date of Patent: Feb. 1, 2000

[54] BONE JOINING DEVICE

[75] Inventors: Saburo Nakamura; Morishige Hata; Takashi Nishiyama; Kenji Narita; Toru Yamamoto; Yasuyuki Kishida; Toru Arima, all of Ayabe, Japan

[73] Assignee: Gunze Limited, Kyoto, Japan

[21] Appl. No.: 09/006,493

[22] Filed: Jan. 13, 1998

[51] Int. Cl.[7] .................................................. A61B 17/56
[52] U.S. Cl. .............................. 606/77; 606/72; 523/105; 523/115
[58] Field of Search .................................. 606/72, 73, 75, 606/76, 77; 523/105, 113, 114, 115

[56] References Cited

U.S. PATENT DOCUMENTS

| | | |
|---|---|---|
| 4,539,981 | 9/1985 | Tunc ........................................ 128/92 |
| 4,550,449 | 11/1985 | Tunc ........................................ 623/16 |
| 4,671,280 | 6/1987 | Dorband et al. ........................ 128/334 |
| 4,781,183 | 11/1988 | Casey et al. ............................. 606/76 |
| 4,898,186 | 2/1990 | Ikada et al. .............................. 606/62 |
| 4,968,317 | 11/1990 | Törmälä et al. .......................... 606/77 |
| 5,007,939 | 4/1991 | Delcommune et al. ................. 623/66 |
| 5,227,412 | 7/1993 | Hyon et al. ............................. 523/105 |
| 5,431,652 | 7/1995 | Shimamoto et al. ..................... 606/76 |

FOREIGN PATENT DOCUMENTS 0 321 176 A2  6/1989  European Pat. Off. .

*Primary Examiner*—Michael Buiz
*Assistant Examiner*—David O. Reip
*Attorney, Agent, or Firm*—Kubovcik & Kubovcik

[57] ABSTRACT

The present invention provides a bone joining device used for joining, fixing and reinforcing fractured bones. The bone joining device is produced by pressing a molded product of a biodegradable and bioabsorbable resin.

14 Claims, 1 Drawing Sheet

BONE JOINING DEVICE

TECHNICAL FIELD

The present invention relates to a bone joining device used for joining, fixing and reinforcing fractured bones.

BACKGROUND ART

In recent years, polylactic acid, polyglycolic acid, a copolymer of lactic acid and glycolic acid and like biodegradable and bioabsorbable polymers are applied to bone joining devices as substitute material for metals, ceramics etc. Since a bone joining material made up of such material is hydrolyzed and absorbed in vivo, there is no need after operation to remove the bone joining material by an additional operation, thereby advantageous. In contrast, a biodegradable and bioabsorbable bone joining device has drawbacks of low tensile strength and flexural strength in comparison with metals, ceramics and the like.

U.S. Pat. No. 4,898,186, U.S. Pat. No. 5,431,652, etc. propose to improve strength and maintenance of the polymer by molecular orientation of the polymer according to a variety of drawing techniques resulting in elevation of crystallinity thereof. Similarly, U.S. Pat. No. 4,743,257 proposes to use, as material thereof, the polymer whose functions are improved by blending a fibrous biodegradable and bioabsorbable polymer with the biodegradable and bioabsorbable polymer. However, further improvements in initial strength and maintenance of strength in vivo are requested.

DISCLOSURE OF THE INVENTION

Figure 1:
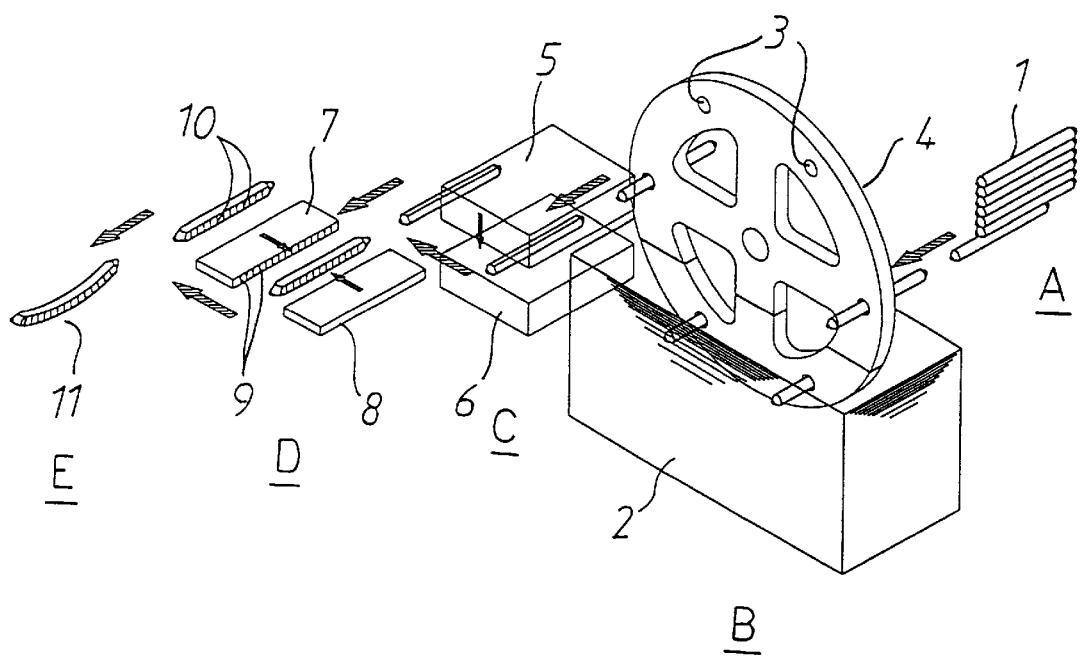
FIG. 1 is an example of manufacturing process of the bone joining device of the invention. Within the Figure, 1 represents material to be molded; 2 represents an oil bath; 3 represents an opening; and 4 represents an rotating disc. 5, 6, 7 and 8 represent a mold. 9 represents a convex part; 10 represents a channel and 11 represents a costal pin as bone joining device.

The present invention relates to a bone joining device wherein a molded product of biodegradable and bioabsorbable resin is pressed.

The molded product includes a drawn molded product and a fibrillated molded product.

The biodegradable and bioabsorbable resin includes a composite material in which biodegradable and bioabsorbable fiber and the resin are mixed. The fiber may be a different material from the resin as long as the fiber is biodegradable and bioabsorbable.

Press working may be conducted at a temperature between glass transition point and melting point of the biodegradable and bioabsorbable resin.

The biodegradable and bioabsorbable resin may be selected from polylactic acid (L form, D form, blend of poly-L-lactic acid and poly-D-lactic acid, or, a copolymer of L-lactic acid and D-lactic acid, stereo complex (polymer of racemic lactic acid), etc.), polyglycolic acid, said copolymer of lactic acid and glycolic acid, blend of polylactic acid and polyglycolic acid and so on having a viscosity-average molecular weight of about tens of thousands to one million. Polylactic acid, in particular, poly-L-lactic acid, or, a copolymer of L-lactic acid and glycolic acid are preferable because of slow degradation which is suitable for the use application. In addition, hydroxyapatite and like bioceramics exerting a favorable influence on regeneration of bone may be blended.

The molded product used for manufacturing the bone joining device of the invention may be produced by any method such as fluxing, injecting said polymer. The molded product may be subjected to press working after stretching or hydrostatic extrusion at a draw ratio of about 2–15.

The molded product may be produced by methods disclosed in U.S. Pat. No. 4,898,186 and U.S. Pat. No. 5,431,652, and by rolling with planetary slant rolling mill (PSW). The molded product may be a molded product in which a fibrous material comprising biodegradable and bioabsorbable polymer is blended with a biodegradable and bioabsorbable polymer as disclosed in U.S. Pat. No. 4,743,257.

The bone joining device of the invention may be produced by press working of molded product comprising biodegradable and bioabsorbable resin around which biodegradable and bioabsorbable fibers are wound.

The molded product, which comprises a molded product of biodegradable and bioabsorbable resin blended with biodegradable and bioabsorbable fibers, may be produced by combination of biodegradable materials with different properties such as degradability and strength, for example, by using molded product having high strength as core and material having inferior strength as covering material.

According to the invention, press working means processing into a desired shape by applying pressure, specifically processing into screw, pin, rod, plate, nail, etc., by applying pressure in one or more directions for shaping. Examples of the press working include filling in a heated mold a biodegradable and bioabsorbable resin to which pressure is applied, and, processing into a desired shape by pressing heated molding tools onto both side of molded product.

Pressure of press working is varied depending on material, size and strength of molded product, but usually about 100 kgf/cm$^2$ to about 900 kgf/cm$^2$.

Time period of press working is varied depending on material, size and strength of a molded product, but usually about 10 seconds to about 90 seconds.

Heating temperature which is an important factor of the press working ranges from glass transition point to melting point of the biodegradable and bioabsorbable resin molded product. When press working is conducted at higher temperature than necessary, molecular weight of the polymer is decreased resulting in exerting adverse effects on strength and degradability thereof, thereby not preferable.

The bone joining device of the invention is easily manufactured, and superior to a device produced by cutting in productivity and decrease of loss, and also in assurance of initial strength and maintenance thereof.

The present invention will be described below in detail with examples. However, the invention is in no way limited to the examples.

Example 1 and comparative example 1

Pellets of poly-L-lactic acid having a viscosity-average molecular weight of 120,000 were subjected to an injection molding machine, fluxed and kneaded for extrusion to give cylindrical molded product. The molded product was subjected to a hydrostatic extruder in which glycerin was filled for drawing by extrusion at a temperature of 130° C. and a extrusion rate of 4 mm/min to obtain cylindrical extruded molded product having a diameter of 3.2 mm and a extrusion ratio of 4. The extruded molded product thus obtained had a flexural strength of 20 kgf/mm$^2$ in contrast with 15 kgf/mm$^2$ before extrusion.

Subsequently, the extruded molded product was cut to 4 cm in length, both ends of the molded product were formed into cone by cutting with a lathe, and then subjected to steps briefly disclosed in FIG. 1 to obtain the pin-like bone joining device for costa of the invention.

Processing is described in further detail based on FIG. 1. In FIG. 1, A is a feed unit of molding material 1, which is fed into a preheater B for preheating. The preheater comprises a rotating disc 4 with an opening 3 to maintain molding material 1 at regular intervals and an oil bath 2. The feed unit is operated to dip one molding material into the oil bath heated at 120° C. for 30 seconds. The preheated molding material is fed into first molding equipment C where mold tools 5, 6 heated at 120° C. are pressed against molded product on upper and lower sides at a pressure of 400 kgf for 30 seconds of press time to form flat surfaces on both upper and lower sides. The molded product is then fed into second molding equipment D where mold tools 7, 8 heated at 120° C. are pressed against the molded product on left and right sides at a pressure of 400 kgf for 30 seconds of press time to form flat surfaces on both left and right sides. The mold tools 7, 8 have convex parts 9 with a height of 1 mm at constant intervals to form irregularity on the surface of the molded product, wherein channels 10 with substantially the same depth are formed at corresponding positions.

As shown above, prism-like pressed molded product having irregularity at constant intervals is obtained. The molded product is further put into a crook-shape chase for heat-setting at 120° C. for 15 minutes to obtain a costa joining pin 11 of the invention having irregular faces for inhibition of falling off and a crook shape to fit the shape of costa.

The pin of the invention thus obtained and a pin of comparative example 1 formed by cutting all faces of said molded product including irregularity with a lathe after extrusion were subjected to in vitro test to determine change of strength with time. The in vitro test was conducted by dipping the pins into phosphate buffered saline (PBS) containing 0.9% by weight of sodium chloride at 50° C. for 1–4 weeks to determine flexural strength after 0, 1, 2, 3 and 4 weeks of dipping. In table 1, a retention rate of strength shown in parentheses is a ratio of strength after 1–4 weeks to initial strength (0 week). The results are shown in table 1.

The flexural strength was determined according to JIS K 7203. All values in table 1 are an average value (n=3).

In table 1, the upper column shows flexural strength (kgf/mm$^2$) and the lower column shows a retention rate of flexural strength.

TABLE 1

| | Dipping period (week) | | | | |
| --- | --- | --- | --- | --- | --- |
| | 0 | 1 | 2 | 3 | 4 |
| Example 1 | 22.2 (100%) | 22.3 (100.5%) | 21.5 (96.8%) | 21.8 (98.2%) | 18.9 (85.1%) |
| Comparative Example 1 | 20.1 (100%) | 19.8 (98.5%) | 20.3 (101.0%) | 19.6 (97.5%) | 13.1 (65.2%) |

As shown in table 1, the product of the invention has higher initial strength and superior retention thereof to the product of comparative example 1 produced by cutting.

In the example, an oil bath is used for preheat during molding, dry heat treatment with a heater may be applied to. Dimensional resistance of molded product may be improved by annealing the drawn product at a temperature between glass transition point and melting point thereof before the preheat treatment.

The bone joining device of the invention which is not only easily produced but also improved in performance may be suitably applied to the bone-joining application, demanding initial strength and retention of performance for relatively long period of time. In addition, fibrillated product or composite with fibers solve the problems of decrease of strength caused by shaving fibrils or fibers, and loss of shape such as loss of thread by peeling fibrils and fibers during shaping of screw, etc. The pressing leads to decreased loss of material and economical.

Pin, plate, rod and like relatively simple shape of bone joining device of the invention is, in particular, preferable.

We claim:

1. A method for producing a bone joining device, which comprises the steps of:

(1) drawing a molded product of a biodegradable and bioabsorbable resin to produce a drawn molded product, (2) preheating the drawn molded product to produce a preheated molded product, and (3) pressing the preheated molded product on upper and lower sides and on left and right sides at a temperature between the glass transition point and the melting point of the molded product of said biodegradable and bioabsorbable resin.

2. The method according to claim 1, wherein the bone joining device retains a flexural strength after a lapse of 4 weeks at a retention rate of at least 85.1% based on initial strength.

3. A bone joining device prepared by the method of claim 2.

4. The method according to claim 1, wherein press working in the step (3) is conducted for 10 to 90 seconds.

5. A bone joining device prepared by the method of claim 4.

6. The method acc ording to claim 1, wherein the drawn molded product is fibrillated.

7. A bone joining device prepared by the method of claim 6.

8. The method according to claim 1, wherein the molded product of biodegradable and bioabsorbable resin is a composite of the biodegradable and bioabsorbable resin and a biodegradable and bioabsorbable fiber.

9. A bone joining device prepared by the method of claim 8.

10. The method according to claim 1, wherein the molded product of biodegradable and bioabsorbable resin is a composite comprising biodegradable and bioabsorbable resins having different properties.

11. A bone joining device prepared by the method of claim 10.

12. The method according to claim 1, wherein the bone joining device is a screw, pin, rod, plate or nail.

13. A bone joining device prepared by the method of claim 12.

14. A bone joining device prepared by the method of claim 1.

* * * * *